US012052987B2

(12) United States Patent
Potenziano et al.

(10) Patent No.: US 12,052,987 B2
(45) Date of Patent: Aug. 6, 2024

(54) ADMINISTRATION AND MONITORING OF NITRIC OXIDE IN EX VIVO FLUIDS

(71) Applicant: Mallinckrodt Pharmaceuticals Ireland Limited, Dublin (IE)

(72) Inventors: Jim Potenziano, Binghamton, NY (US); Douglas R. Hansell, Easton, PA (US); Jeff Griebel, Arora, CO (US); Eddie Costa, San Diego, CA (US); Lisa Cooper, Upper Black Eddy, PA (US); David William Newman, Lebanon, NJ (US)

(73) Assignee: Mallinckrodt Pharmaceuticals Ireland Limited, Dublin (IE)

( * ) Notice: Subject to any disclaimer, the term of this patent is extended or adjusted under 35 U.S.C. 154(b) by 22 days.

(21) Appl. No.: 17/863,778

(22) Filed: Jul. 13, 2022

(65) Prior Publication Data
US 2022/0354110 A1 Nov. 10, 2022

Related U.S. Application Data

(63) Continuation of application No. 16/856,632, filed on Apr. 23, 2020, now Pat. No. 11,412,731, which is a continuation of application No. 15/066,672, filed on Mar. 10, 2016, now Pat. No. 10,667,510, which is a continuation-in-part of application No. 14/556,364, filed on Dec. 1, 2014, now abandoned, which is a continuation-in-part of application No. 14/095,621, filed on Dec. 3, 2013, now Pat. No. 9,629,358.

(60) Provisional application No. 61/787,865, filed on Mar. 15, 2013.

(51) Int. Cl.
*A01N 1/02* (2006.01)
*A61M 1/16* (2006.01)
*A61M 1/36* (2006.01)
*A61M 16/10* (2006.01)

(52) U.S. Cl.
CPC ......... *A01N 1/0247* (2013.01); *A01N 1/0226* (2013.01); *A61M 1/1698* (2013.01); *A61M 1/3623* (2022.05); *A61M 2016/1035* (2013.01); *A61M 2202/0275* (2013.01); *A61M 2230/30* (2013.01); *A61M 2230/437* (2013.01)

(58) Field of Classification Search
None
See application file for complete search history.

(56) References Cited

U.S. PATENT DOCUMENTS

| | | |
|---|---|---|
| 5,338,662 A | 8/1994 | Sadri |
| 5,558,083 A | 9/1996 | Bathe et al. |
| 5,732,693 A | 3/1998 | Bathe et al. |
| 5,752,504 A | 5/1998 | Bathe |
| 6,125,846 A | 10/2000 | Bathe et al. |
| 6,314,956 B1 | 11/2001 | Stamler et al. |
| 7,238,469 B2 | 7/2007 | Bach et al. |
| 7,523,752 B2 | 4/2009 | Montgomery et al. |
| 8,282,966 B2 | 10/2012 | Baldassarre et al. |
| 8,291,904 B2 | 10/2012 | Bathe et al. |
| 8,293,284 B2 | 10/2012 | Baldassarre et al. |
| 8,431,163 B2 | 4/2013 | Baldassarre et al. |
| 8,573,209 B2 | 11/2013 | Bathe et al. |
| 8,573,210 B2 | 11/2013 | Bathe et al. |
| 8,776,794 B2 | 7/2014 | Bathe et al. |
| 8,776,795 B2 | 7/2014 | Bathe et al. |
| 8,795,741 B2 | 8/2014 | Baldassarre |
| 8,846,112 B2 | 9/2014 | Baldassarre |
| 2002/0133068 A1 | 9/2002 | Huiku |
| 2004/0081580 A1 | 4/2004 | Hole et al. |
| 2004/0092805 A1 | 5/2004 | Yarita |
| 2004/0122301 A1 | 6/2004 | Kiani et al. |
| 2004/0224298 A1 | 11/2004 | Brassil et al. |
| 2009/0197240 A1 | 8/2009 | Fishman et al. |
| 2010/0285100 A1 | 11/2010 | Balkus, Jr. et al. |
| 2011/0059036 A1 | 3/2011 | Arnold et al. |
| 2011/0136096 A1 | 6/2011 | Hassanein et al. |
| 2012/0201906 A1 | 8/2012 | Reynolds et al. |
| 2014/0275901 A1 | 9/2014 | Flanagan et al. |
| 2015/0151034 A1 | 6/2015 | Goldstein et al. |

FOREIGN PATENT DOCUMENTS

| | | |
|---|---|---|
| JP | 2008525499 A | 7/2008 |
| WO | 2013070712 A1 | 5/2013 |

OTHER PUBLICATIONS

Nakagawa, A., et al. "Real-time monitoring of liver damage during experimental ischaemia-reperfusion using a nitric oxide sensor." Journal of British Surgery 99.8 (2012): 1120-1128. (Year: 2012).*
Morandi, L., et al. "High plasma creatine kinase: review of the literature and proposal for a diagnostic algorithm." Neurological Sciences 27 (2006): 303-311. (Year: 2006).*
Abstract of JP2008525499 from www.espacenet.com, Jul. 17, 2008, 1 page.
Aitchinson J.D., et al., "Nitric Oxide During Perfusion Improves PostTransplantation Function of Non-Heart-Beating Donor Lungs," Transplantation, Jun. 27, 2003, vol. 75 (12), pp. 1960-1964.
Brian K.J., et al., "Circulating Methemoglobin and Nitrite/Nitrate Concentrations as Indicators of Nitric Oxide Overproduction in Critically ill Children with Septic Shock," Critical Care Medicine, 1997, vol. 25, No. 9, pp. 1588-1593.

(Continued)

*Primary Examiner* — Robert J Yamasaki

(57) ABSTRACT

Described are systems and methods for monitoring administration of nitric oxide (NO) to ex vivo fluids. Examples of such fluids include blood in extracorporeal membrane oxygenation (ECMO) circuits or perfusion fluids used for preserving ex vivo organs prior to transplanting in a recipient. The systems and methods described herein provide for administering nitric oxide to the fluid, monitoring nitric oxide or a nitric oxide marker in the fluid, and adjusting the nitric oxide administration.

15 Claims, 4 Drawing Sheets

(56) References Cited

OTHER PUBLICATIONS

Hamirani Y.S., et al., "Methemoglobinemia in a Young Man," Texas Heart Institute Journal, 2008, vol. 35 (1), pp. 76-77.
Hermle G., et al., "Ventilation-Perfusion Mismatch after Lung Ischemia-Reperfusion," Protective Effect of Nitrix Oxide, American Journal of Respiratory and Critical Care Medicine, 1999, vol. 160, pp. 1179-1187.
INOmax DS (Delivery System): Operation Manual (800 ppm INOMAX (nitric oxide) for Inhalation), Ikaria, Inc. 2010, 112 Pages.
INOmax DSIR (Delivery System): Operation Manual (800 ppm INOMAX (nitric oxide) for Inhalation), Ikaria, Inc. 2012, 136 Pages.
INOmax Label, Nitric Oxide Gas, INO Therapeutics 2013, 2 Pages.
INOvent Delivery System: Operation and Maintenance Manual (CGA Variant), Datex-Ohmeda, Inc. 2000, 180 Pages.
International Search Report for International Application No. PCT/US2014/067856, dated Aug. 26, 2015, 17 pages.
Ishibe Y., et al., "Role of Inhaled Nitric Oxide in Ischaemia-Reperfusion Injury in the Perfused Rabbit Lung," British Journal of Anaesthesia, ISSN 0007-0912, 1999, vol. 83 (3), pp. 430-435.
Kageyama S., et al., "Graft Reconditioning With Nitric Oxide Gas in Rat Liver Transplantation From Cardiac Death Donors," Transplantation, Mar. 27, 2014, vol. 97 (6), pp. 618-625.
Lowson S.M., et al., "The Effect of Nitric Oxide on Platelets When Delivered to the Cardiopulmonary Bypass Circuit," Anesthesia & Analgesia, Society of Cardiovascular Anesthesiologists, 1999, vol. 89, pp. 1360-1365.
*Mallinckrodt Hospital Products IP Ltd et al v. Praxair Distribution Inc et al*, 1:15-cv-00170, Sep. 5, 2017, 45 pages.
Menezes A.Q., et al., "Comparison of Celsior and Perfadex Lung Preservation Solutions in Rat Lungs Subjected to 6 and 12 Hours of Ischemia Using an Ex-Vivo Lung Perfusion System," Clinics, 2012, vol. 67 (11), pp. 1309-1314.
Murakami S., et al., "Effects of Various Timings and Concentrations of Inhaled Nitric Oxide in Lung Ischemia-Reperfusion," American Journal of Respiratory and Critical Care Medicine, 1997, vol. 156, pp. 454-458.

Nagai K., et al., "Impact of Venous-Systemic Oxygen Persufflation With Nitric Oxide Gas on Steatotic Grafts After Partial Orthotopic Liver Transplantation in Rats," Transplantation, Jan. 15, 2013, vol. 95 (1), pp. 78-84.
Office Action for Australian Patent Application No. 2014357412, dated Aug. 8, 2017, 06 pages.
Office Action for Canadian Application No. 3,135,254, mailed on Oct. 31, 2022, 3 pages.
Office Action for European Patent Application No. 14824182.1, mailed Jul. 20, 2018, 12 pages.
Office Action for European Patent Application No. 14824182.1, mailed Sep. 14, 2017, 08 pages.
Office Action for Japanese Patent Application No. 2016-536173, dated Oct. 9, 2018, 08 pages.
Okamoto T., et al., "Nebulized Nitrite Protects Rat Lung Grafts from Ischemia Reperfusion Injury," The Journal of Thoracic and Cardiovascular Surgery, 2012, vol. 145 (4), pp. 1108-1116.
PCT Annex to Form PCT/ISA/206 Communication Relating to the Results of the Partial Search Report in PCT/US2014/067856, dated Mar. 26, 2015, 9 pages.
Srinivasan P.K., et al., "Impact of Venous Systemic Oxygen Persufflation Supplemented With Nitric Oxide Gas on Cold-Stored, Warm Ischemia-Damaged Experimental Liver Grafts," Liver Transplantation, Feb. 2012, vol. 18 (2), pp. 219-225.
Stamler J.S., et al., "Nitric Oxide Circulates in Mammalian Plasma Primarily as an S-Nitroso Adduct of Serum Albumin," Proceedings of the National Academy of Sciences, Aug. 1992, vol. 89 (16), pp. 7674-7677.
Using the INOpulse DS Subject Guide, Ikaria, Inc. 2012, 50 Pages.
Wittwer T., et al., "Experimental Lung Preservation with Perfadex: Effect of the NO-Donor Nitroglycerin on Postischemic Outcome," The Journal of Thoracic and Cardiovascular Surgery, Cardiothoracic Transplantation, Jun. 2003, vol. 125 (6), pp. 1208-1216.
Yagi S., et al., "A Novel Organ Preservation for Small Partial Liver Transplantations in Rats: Venous Systemic Oxygen Persufflation With Nitric Oxide Gas," American Journal of Transplantation, 2013, vol. 13, pp. 222-228.

* cited by examiner

ADMINISTRATION AND MONITORING OF NITRIC OXIDE IN EX VIVO FLUIDS

CROSS-REFERENCE TO RELATED APPLICATIONS

This application is a continuation of U.S. patent application Ser. No. 16/856,632, filed Apr. 23, 2020 which is a continuation of U.S. patent application Ser. No. 15/066,672, filed Mar. 10, 2016 which is a continuation-in-part under 35 U.S.C. § 120 of U.S. patent application Ser. No. 14/556,364, filed Dec. 1, 2014, which claims the benefit under 35 U.S.C. § 120 of U.S. patent application Ser. No. 14/095,621, filed Dec. 3, 2013, which claims the benefit under 35 U.S.C. § 119(e) of U.S. Provisional Application No. 61/787,865, filed Mar. 15, 2013, the entire contents of which is incorporated herein by reference in their entirety.

TECHNICAL FIELD

Embodiments of the present invention generally relate to the field of methods and devices for delivering and monitoring nitric oxide (NO). In particular, embodiments of the present invention relate to the use of NO in the contexts of extra corporeal membrane oxygenation (ECMO) systems and organ and tissue preservation.

BACKGROUND

Cells, tissues, organs, and organisms that are deprived of appropriate blood flow undergo ischemic damage. Traditional methods of reducing ischemic damage involve perfusing affected tissues with oxygen, but this procedure can cause significant tissue damage and can result in serious and/or permanent injury, such as brain damage during stroke or cardiac arrest.

Attempts have been made to reduce ischemia-reperfusion injury (IRI) by inducing tissues and organs to enter a reduced metabolic state. In the context of living tissues being preserved for transplant or grafting, one common method for reducing their metabolic activity is by immersing tissues or organs in a physiologic fluid, such as saline, and placing them in a cold environment. However, such methods cannot be relied upon for extended periods, and the success of organ and tissue transplant and limb reattachments remains inversely related to the time the organ, tissue or limb is out of contact with a living organism. Accordingly, there is a need for improved methods of preserving organs, tissues, limbs and other biological materials.

Separately, oxygen deprivation can also occur in living organisms when the lungs are improperly functioning or not functioning at all. One approach to improving oxygenation in patients is through the use of ECMO, in which venous blood is extracted from the patient, passed through a membrane oxygenator, and then returned to the patient. The ECMO system may include filters or other components which are used to remove blood clots and other biological materials that may need removal before blood is reintroduced into the patient thereby avoiding clogging of the ECMO system, in particular clogging of the membrane oxygenator. There is a need to improve existing ECMO systems and methods to avoid this clogging.

SUMMARY

Embodiments of the present invention provide methods and systems for administering NO-containing gas directly to ex vivo fluid, as well as monitoring NO and/or a NO marker and/or other relevant parameter (e.g. indicators of tissue damage) in the ex vivo fluid and/or in tissues or organs that receive the ex vivo fluid. The methods and systems described herein may be utilized for a variety of purposes, including prevention and treatment of ischemia-reperfusion injury and for preventing blood clots in an ECMO circuit. The NO may be administered to various biological materials, including cells, tissues, organs, organisms, and animals, including humans and other mammals.

Although the methods and systems described herein have many applications, in particular it is believed that the administration of NO and the monitoring thereof are beneficial in the context of ECMO circuits and/or the preservation of organs and other biological material for transplantation. With respect to ECMO, in which a patient blood's is oxygenated ex vivo, NO is added to the ECMO circuit and NO and/or a NO marker is monitored, and the NO administration is adjusted accordingly. Without wishing to be bound by any particular theory, it is expected that NO administration to blood in an ECMO circuit will reduce platelet activation in the blood, and thus help prevent clogging in the ECMO circuit. For example, a filter in the ECMO circuit may become clogged due to the aggregation of platelets, and the filter may have to be replaced, which is expensive and inconvenient. Accordingly, NO administration may be used to prevent clogs thereby extending the life of the ECMO circuit. However, excess NO may result in the formation of methemoglobin, which does not bind oxygen, and can lead to methemoglobinemia. As a result, NO administration may be monitored to ensure that the methemoglobin or other NO marker does not rise above or below a certain safety threshold.

With respect to organ and biological material transplant, an organ is removed from a donor and significant efforts are made to appropriately preserve the organ or biological material for implantation into a recipient. Biological materials, including cells, tissues and organs, that are used for transplantation require effective ex vivo preservation from the moment the organ or other biological material is retrieved to the time of transplantation. Organ transplantation includes many methods that may be used individually or in combination. In one or more methods, NO is administered to perfusion fluid, and NO and/or a NO marker and/or other relevant parameter is monitored in the perfusion fluid and the amount of NO being administered is adjusted if necessary in order to meet or maintain an appropriate amount of NO. Alternatively or in addition to monitoring the perfusion fluid, the organ or tissue may be monitored directly, such as by measuring NO and/or a NO marker and/or other parameters (such as indicators of tissue damage) in the organ or tissue. NO may also be added to gases used to persufflate an organ or to gases used to ventilate ex vivo lungs. It is expected that NO administration to perfusion fluids, persufflation gases, and ventilation gases, and the monitoring thereof, will extend organ donor pool and increase viability of donated organs. NO may be used as a preconditioning agent to limit organ damage from ischemia-reperfusion injury. NO is expected to help with organ preservation at least in part by reducing the warm ischemia "hit" which occurs when blood is re-perfused to an organ post-transplant. While not wishing to be bound by any particular theory, it is believed that this reduction in warm ischemia hit may occur by multiple mechanisms, including reduction in oxidative stress and/or preservation of key cellular function.

Furthermore, NO administration may also reduce microcirculation alterations that can occur after removing an organ for transplant and/or during/following ECMO. For example, after an organ is removed, the microcirculation of the organ can undergo restructuring, which can greatly affect perfusion through the organ. The more restructuring that occurs, the poorer the prognosis for the organ transplant. NO may be used to treat and/or prevent such microcirculation alteration, such as by administering NO, monitoring microcirculation and adjusting the NO administration in response to microcirculation alterations.

Accordingly, one aspect of the present invention is directed to a method of monitoring NO administration. In one or more embodiments, this method comprises administering NO to an ex vivo fluid, monitoring NO and/or a NO marker and/or other relevant parameter in the ex vivo fluid and adjusting the NO administration based on the monitoring of the NO and/or NO marker and/or other relevant parameter. The ex vivo fluid may contain components such as red blood cells, etc. Administrating NO to the ex vivo fluid may comprise contacting the ex vivo fluid with a gas comprising a NO concentration in the range from 0.1 ppm to 300 ppm. The ex vivo fluid can be contacted with cells after administrating NO to the fluid or during administration of NO to the ex vivo fluid. As set forth above, NO and/or a NO marker and/or other relevant parameter may also be measured in an organ or tissue, in addition to or as an alternative to measuring NO and/or a NO marker and/or other relevant parameter in the ex vivo fluid.

In one or more embodiments, the ex vivo fluid comprises one or more of blood or perfusion fluid. The ex vivo fluid may comprise blood that is recirculated in an extracorporeal membrane oxygenation (ECMO) circuit and, the ex vivo blood may be introduced into a living organism (such as a human) so that the blood may contact cells in the living organism. As an alternative example, the ex vivo fluid may comprise perfusion fluid and the cells that are contacted with the ex vivo fluid may comprise ex vivo organ cells.

The ex vivo fluid may also be oxygenated before administrating NO to the ex vivo fluid and/or after administrating NO to the ex vivo fluid. The NO and/or NO marker and/or other parameter may be monitored before oxygenating the ex vivo fluid, after oxygenating the ex vivo fluid and before administering NO to the ex vivo fluid, after administering NO to the ex vivo fluid and before contacting the cells with the ex vivo fluid, and/or after contacting the cells with the ex vivo fluid.

The NO monitoring may be performed continuously or intermittently and the nitric oxide administration may be adjusted continuously or intermittently. In one or more embodiments, monitoring the NO marker comprises one or more of monitoring methemoglobin in the ex vivo fluid or monitoring NOx in the ex vivo fluid. In one or more embodiments, adjusting the NO administration comprises adjusting one or more of the NO concentration or the flow rate of the gas comprising NO that is delivered to the ex vivo fluid.

Another aspect of the present invention relates to a method of monitoring NO administration during extracorporeal membrane oxygenation (ECMO). In one or more embodiments, this method comprises administering NO to ex vivo blood in an ECMO circuit by contacting the ex vivo blood with a gas comprising a NO concentration in the range from 1 ppm to 50 ppm, monitoring one or more of (1) a pressure drop in the ECMO circuit to determine if the pressure drop is above a pressure drop threshold or (2) NO and/or a NO marker in the ex vivo blood to determine if the NO and/or NO marker is below or above a NO threshold, and adjusting the NO administration based on one or more of the monitoring of the pressure drop or the monitoring of the NO and/or NO marker. The NO administration may be increased if the pressure drop is above the pressure drop threshold and the NO administration may be decreased if the NO and/or NO marker is above the NO threshold.

In one or more embodiments, the pressure drop threshold is in the range from 1% to 30% of the maximum pressure in the ex vivo circuit.

In one or more embodiments, adjusting the NO administration comprises adjusting one or more of the NO concentration or the flow of the gas comprising NO.

In one or more embodiments, monitoring the NO marker comprises one or more of monitoring methemoglobin in the ex vivo blood or monitoring NOx in the ex vivo blood. Monitoring the NO marker may comprise monitoring methemoglobin and the NO threshold may be in the range from 1% to 15% methemoglobin. In some embodiments, the NO marker is monitored via one or more of pulse oximetry, optical measurement or any other means for measuring or co-relating NO and/or NO markers either directly or indirectly.

Another aspect of the present invention pertains to a method of monitoring NO administration to an ex vivo fluid for biological material preservation. In one or more embodiments, this method comprises administering NO to an ex vivo fluid by contacting the ex vivo fluid with a gas comprising a NO concentration in the range from 0.1 ppm to 300 ppm, monitoring NO and/or a NO marker and/or other parameter in the ex vivo fluid, and adjusting the NO administration based on the monitoring of the NO and/or NO marker and/or other parameter. The biological material may comprise one or more of isolated cells, tissue, a partial organ or a complete organ. In one or more embodiments, the organ comprises one or more of a heart, lung, kidney, liver, pancreas, eye, bone, skin, heart valve, bowel, tendon, ligament or vein. In particular embodiments, the organ may be a liver. In other particular embodiments, the organ may be one or more lungs. In other particular embodiments, the organ may be a heart.

In one or more embodiments, monitoring the NO marker comprises one or more of monitoring methemoglobin in the ex vivo fluid or monitoring NOx in the ex vivo fluid. Monitoring the NO marker may comprise monitoring methemoglobin and the NO threshold may be in the range from 1 to 50% methemoglobin.

In one or more embodiments, adjusting the NO administration comprises adjusting one or more of the NO concentration or the flow rate of the gas comprising NO.

Another aspect of the present invention relates to a method of preserving an ex vivo liver for transplant. In various embodiments of this aspect, the method comprises persufflating the liver with a persufflation gas comprising NO, monitoring one or more persufflation parameters in (i) the liver and/or (ii) a preservation fluid used to store the liver during persufflation, and adjusting the amount of NO provided to the liver by the persufflation gas based on the monitoring of the one or more persufflation parameters. In one or more embodiments, the one or more persufflation parameters is selected from the group consisting of NO, a NO marker, an indicator of tissue damage, and combinations thereof. Examples of indicators of tissue damage include, but are not limited to, aspartate aminotransferase (AST) and alanine aminotransferase (ALT).

In one or more embodiments, the concentration of NO in the persufflation gas is in the range from 0.1 ppm to 300 ppm. The persufflation gas may contain other gases in addition to NO, such oxygen and/or air and/or carrier gases such as nitrogen and helium.

Monitoring may be performed continuously or intermittently and adjusting the amount of NO and/or the NO donor may be performed continuously or intermittently.

In various embodiments of this aspect, the method further comprises perfusing the liver with a perfusion fluid comprising NO and/or a NO donor. The liver may be perfused with the perfusion fluid before the liver is persufflated with the persufflation gas. In one or more embodiments, one or more perfusion parameters (such as NO and/or a NO marker and/or an indicator of tissue damage) is monitored in the perfusion fluid and/or in the liver itself, and the amount of NO and/or NO donor provided to the liver by the perfusion fluid is adjusted based on the monitoring of the one or more perfusion parameters.

According to one or more embodiments, adjusting one or more of (i) the amount of NO provided to the liver by the persufflation gas or (ii) the amount of NO provided to the liver by the perfusion fluid comprises adjusting the NO concentration in a flow of gas delivered to the persufflation gas and/or perfusion fluid, and/or adjusting the flow rate of the gas delivered to the persufflation gas and/or perfusion fluid.

The perfusion fluid may comprise red blood cells, and the method may further comprise oxygenating the perfusion fluid before perfusing the liver. In some embodiments, monitoring the NO marker in the perfusion fluid comprises monitoring methemoglobin.

In some embodiments, the viability of the liver is increased by the persufflation and/or perfusion with NO and/or NO donor, particularly when the NO administration is adjusted based on the monitoring as described herein.

Another aspect of the present invention pertains to a method of preserving an ex vivo lung for transplant. In various embodiments of this aspect, the method comprises perfusing the lung with a perfusion fluid comprising NO and/or a NO donor, and/or ventilating the lung with a ventilation gas comprising NO. The method may also comprise monitoring one or more parameters of the perfusion fluid and/or monitoring one or more parameters of the ventilation gas and/or monitoring one or more parameters of the lung, and adjusting one or more of (i) the amount of NO and/or NO donor provided to the lung by the perfusion fluid based on the monitoring of the one or more parameters of the perfusion fluid and/or the monitoring of the one or more parameters of the lung, or (ii) the amount of NO provided to the lung by the ventilation gas based on the monitoring of the one or more parameters of the ventilation gas and/or the monitoring of the one or more parameters of the lung. In one or more embodiments, the one or more parameters of the perfusion fluid is selected from the group consisting of NO, a NO marker, an indicator of tissue damage, and combinations thereof. In one or more embodiments, the one or more parameters of the ventilation gas is selected from the group consisting of NO, NO2, and combinations thereof. In one or more embodiments, the one or more parameters of the lung is selected from the group consisting of NO, a NO marker, an indicator of tissue damage, a pulmonary parameter, and combinations thereof.

In exemplary embodiments, pulmonary vascular resistance is monitored and the amount of NO provided to the lung by the ventilation gas is adjusted based on the monitoring of pulmonary vascular resistance.

In one or more embodiments, the concentration of NO in the ventilation gas is in the range from 0.1 ppm to 300 ppm. The ventilation gas may contain other gases in addition to NO, such oxygen and/or air and/or carrier gases such as nitrogen and helium. For example, the ventilation gas can have at least 20% oxygen.

The lung may be perfused and ventilated simultaneously, or the perfusion and ventilation may be sequential. The perfusion and ventilation may also occur for different lengths of time.

In some embodiments, the perfusion fluid comprises red blood cells. Monitoring the NO marker in the perfusion fluid may comprise monitoring methemoglobin.

As described above, monitoring may be performed continuously or intermittently and adjusting the amount of NO and/or the NO donor may be performed continuously or intermittently.

In one or more embodiments, adjusting one or more of (i) the amount of NO provided to the lung by the perfusion fluid or (ii) the amount of NO provided to the lung by the ventilation gas adjusting the NO concentration in a flow of gas delivered to the ventilation gas and/or perfusion fluid, and/or adjusting the flow rate of the gas delivered to the ventilation gas and/or perfusion fluid.

In some embodiments, the viability of the lung is increased by the ventilation and/or perfusion with NO and/or NO donor, particularly when the NO administration is adjusted based on the monitoring as described herein.

Also provided is a system for delivering and monitoring NO. In one or more embodiments, the system comprises a NO delivery device for administering NO to an ex vivo fluid such as perfusion fluid, persufflation gas and/or ventilation gas. The system may also comprise a monitoring device for monitoring NO and/or a NO marker and/or other relevant parameter in the ex vivo fluid, in an organ, or in the environment of the organ. The monitoring device may be in communication with the NO delivery device, and the NO delivery device may adjust the NO administration based on the monitoring of the NO and/or NO marker and/or other parameter. The monitoring device may be part of or integrated with the NO delivery device, or it may be a separate component from the NO delivery device.

In one or more embodiments, administrating NO comprises contacting the ex vivo fluid with a gas comprising a NO delivery concentration in the range from 0.1 ppm to 300 ppm. Such NO concentrations can also be used in a persufflation gas and/or ventilation gas.

The monitoring device may comprise any appropriate measurement device, including one or more of a pulse oximeter or an optical measurement device.

In one or more embodiments, the NO delivery device is in communication with a first pressure sensor and a second pressure sensor in an extracorporeal oxygenation (ECMO) circuit that provide a first pressure reading and a second pressure reading, respectively, and the NO delivery device adjusts the NO administration based on a differential between the first pressure reading and the second pressure reading. In some embodiments, the NO delivery device increases the NO administration if the differential between the first pressure reading and the second pressure reading is above 1% to 30% of the first pressure reading.

In one or more embodiments, the NO delivery device adjusts one or more of the NO concentration or the flow of gas comprising NO.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1:
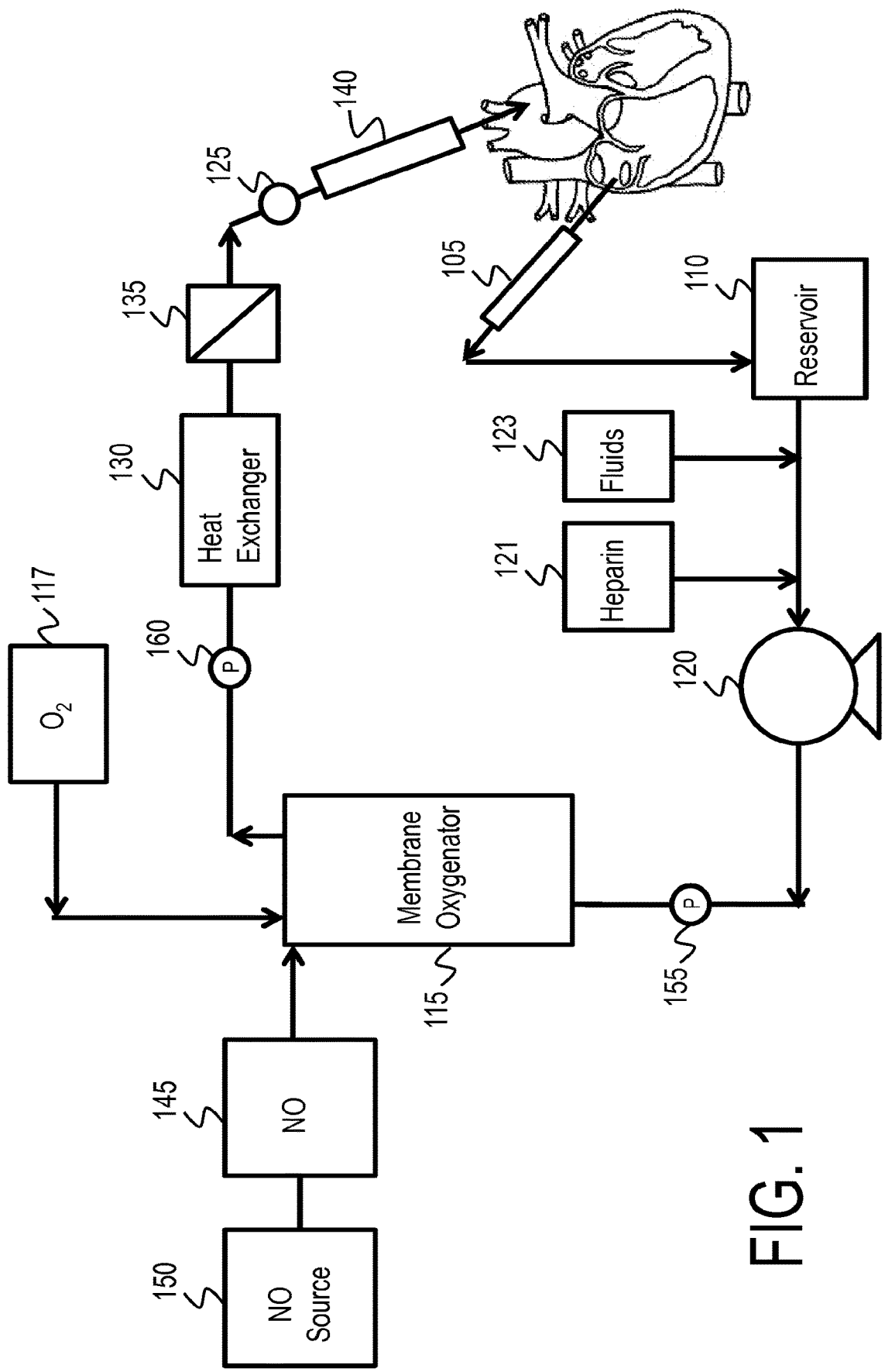
FIG. 1 illustrates an exemplary ECMO circuit that can be used in accordance with one or more embodiments of the invention.

As used in the specification and appended claims, unless specified to the contrary, the following terms have the meaning indicated:

The term "biological material" refers to any living biological material, including cells, tissues, organs, and/or organisms. It is contemplated that the methods of the present invention may be practiced on a part of an organism (such as in cells, in tissue, and/or in one or more organs), or on the whole organism. The term "in vivo biological material" refers to biological material that is in vivo, i.e., still within or attached to an organism. "Ex vivo biological material" includes biological material that is outside of a living organism, such as "ex vivo organs" that are preserved for later transplant into a living organism or grafting onto a living organism.

"Ex vivo fluid" refers to any fluid outside of a living organism. The ex vivo fluid may be a liquid, gas, combinations of different liquids, combinations of different gases, or combinations of liquids or gases. The fluid may provide blood and/or components of blood and/or other components that are beneficial for a biological material. For example, such fluids can contain red blood cells for carrying oxygen to the biological material. Exemplary ex vivo fluids include, but are not limited to, perfusion fluid, ex vivo blood, persufflation gases and ventilation gases. Ex vivo fluid may be taken from a living organism (such as a mammal) or other natural source or can be synthetic, or may be a combination of these sources.

"Delivery concentration" refers to the concentration of NO gas in a composition of NO-containing gas for medical use which is delivered to an ex vivo fluid. In addition to NO gas, such compositions for medical use may further comprise an inert diluent gas. It is to be understood that the delivery concentration will be diluted upon contact with the ex vivo fluid, where it is mixed and distributed to the target biological material.

"NO donor" refers to a compound that donates one or more molecules of nitric oxide (NO). Examples of NO donors known in the art include compounds such as nitroglycerin and sodium nitroprusside.

"NO marker" refers to a direct or indirect indicator of NO concentration in a fluid. For example, NO markers include, among others, methemoglobin and NOx (i.e. NO, nitrite ions ($NO_2-$), nitrate ions ($NO_3-$), etc.).

The term "perfusion fluid" refers to any fluid used in the preservation of ex vivo cells, tissue or organs. Often, perfusion fluids will have compositions similar to blood or contain components found in blood such as red bloods cells, salts, preservatives, etc. However, perfusion fluids do not necessarily need to include red blood cells, and can be any fluid used to preserve organs or cells. For example, the perfusion fluid may be histidine-tryptophan-ketoglutarate solution (available as CUSTODIOL® HTK Solution from Dr. Franz Kohler Chemie GmbH in Germany). Another example of a perfusion fluid is PERFADEX® (available from XVIVO Perfusion AB in Sweden), which is a colloid-containing, lightly-buffered "extracellular" low K+ electrolyte solution. Perfusion fluids are often sterile and isotonic. The composition of the perfusion fluid may vary between organs.

The term "preservation fluid" also refers to any fluid used in the preservation of ex vivo cells, tissue or organs. A preservation fluid may have any of the characteristics of perfusion fluid as described herein. However, a preservation fluid is not required to have the same content as a perfusion fluid, and if an organ is treated with both a preservation fluid and a perfusion fluid, the two fluids may have the same or different compositions.

"Perfusion parameter" refers to any relevant parameter that may monitored or measured during a perfusion process. Examples of such parameters include NO, NO markers, and indicators of tissue damage. Perfusion parameters may be measured in an organ being perfused or in all or a portion of the organ's environment, such as in the fluid used to perfuse the organ.

"Persufflation gas" refers to a gas that is used to persufflate an organ during an ex vivo organ preservation process.

"Persufflation parameter" refers to any relevant parameter that may monitored or measured during a persufflation process. Examples of such parameters include NO, NO markers, and indicators of tissue damage. Persufflation parameters may be measured in an organ being persufflated or in a portion of the organ's environment, such as a preservation fluid used to store the organ during persufflation.

"Pulmonary parameter" refers to any relevant parameter that may monitored or measured that gives an indication of the performance of the pulmonary vasculature. Examples of pulmonary parameters include, but are not limited to, pulmonary vascular resistance (PVR), pulmonary capillary wedge pressure (PCWP), mean pulmonary arterial pressure (mPAP) and cardiac output (CO).

"Ventilation gas" refers to a respiratory gas used to ventilate one or more lungs during preservation of the lungs ex vivo.

"Therapeutically effective amount" refers to that amount of NO gas that, when administered to a subject, organ and/or device, is sufficient to effect treatment as defined herein. The amount of NO which constitutes a "therapeutically effective amount" will vary depending on a variety of factors, but may be determined by one of ordinary skill in the art.

"Treating" or "treatment" as used herein covers the treatment of the disease or condition of interest in a subject or organ of a subject, or the blood of a subject, having the disease or condition of interest, and includes: (i) preventing the disease or condition from occurring in the subject, (ii) inhibiting the disease or condition, i.e., arresting its progression; (iii) relieving the disease or condition, i.e., causing regression of the disease or condition; or (iv) relieving the symptoms resulting from the disease or condition. As used herein, the terms "disease," "disorder," and "condition" may be used interchangeably.

Aspects of the current invention relate to a method of monitoring NO administration comprising administering NO-containing gas to an ex vivo fluid, such as one that contains red blood cells, and monitoring NO and/or a NO marker and/or other parameter in the fluid. The fluid may be oxygenated before and/or after administrating the NO. After administering NO to the fluid and optionally oxygenating the fluid (either before and/or after NO administration), the fluid is transported to and contacted with cells in a biological material. The cells may also be contacted with the ex vivo fluid during administration of NO to the ex vivo fluid. These cells may be isolated cells, tissue, partial organs, complete organs, or may be within a living organism such as a mammal.

The NO-containing gas comprises NO and optionally a carrier gas such as nitrogen, helium and/or air. The NO-containing gas may be provided by any known method, such as from a gas cylinder or chemically generating the NO at or near the place of administration. The NO-containing gas may be at a higher concentration in the cylinder or other gas source and be diluted to a delivery concentration prior to use.

Alternatively, a NO donor may be used instead of or in addition to a NO-containing gas. NO donors are known in the art and include compounds such as nitroglycerin and sodium nitroprusside.

Furthermore, it is also possible to use a fluid that already contains NO and/or a NO donor. In such embodiments, it is not necessary to administer NO and/or a NO donor to the fluid.

In one or more embodiments, the delivery concentration of NO in the NO-containing gas is in the range from 0.1 ppm and 300 ppm.

In one or more embodiments, the NO-containing gas is administered continuously, for example by continuously contacting the ex vivo fluid with the NO-containing gas. The NO-containing gas may also be administered as a "pulse" or series of pulses to the ex vivo fluid. Similarly, the oxygen may be administered either continuously or pulsed. NO and oxygen may also be intermittently pulsed.

A device can be used to monitor NO and/or a NO marker and/or other relevant parameter in the ex vivo fluid and/or used to monitor in the living organism or cells. Such monitoring may comprise monitoring the methemoglobin and/or NOx in the ex vivo fluid. These NO markers may be measured directly through techniques such as pulse oximetry or optical measurement or any other means for measuring or co-relating NO and/or NO markers either directly or indirectly. For example, another measurement technique involves placing a probe in the ex vivo fluid to measure fluid NOx levels and may provide real-time analysis of the ex vivo fluid.

Other monitoring devices can include imaging and/or spectroscopic devices such as computed tomography (CT) devices, magnetic resonance imaging (MIll) devices, nuclear magnetic resonance (NMR) devices, and ultrasound devices. These imaging and/or spectroscopic devices may automatically communicate information to a NO delivery device. These imaging and/or spectroscopic devices may also provide visual imaging that is evaluated by a clinician, who can make manual adjustments to a NO delivery device. For example, the clinician may visually assess circulation and/or tissue composition with the aide of an imaging and/or spectroscopic device to determine if there is tissue damage or other need to adjust the amount of NO provided to the biological material.

The monitoring device may be part of or integrated into the NO delivery device, or the NO and/or NO marker may be monitored by a component separate from the NO delivery device.

In one or more embodiments, the NO administration is adjusted based on the monitoring of the NO and/or NO marker and/or other relevant parameter. Such adjustment may be manual or automatically implemented by the NO delivery device. The NO delivery system may also provide an alarm based on the monitoring. If the monitoring device is a separate component from the NO delivery device, the monitoring device may transmit the monitoring information to the NO delivery device via any appropriate wired or wireless connection. For example, if the NO and/or NO marker and/or other parameter in the fluid is below a certain threshold, NO delivery may be increased until the NO and/or NO marker and/or other parameter in the fluid meets the threshold. Similarly, if the NO and/or NO marker and/or other parameter in the fluid is above a certain threshold, the amount of NO administered may be decreased.

In one or more embodiments, the NO and/or NO marker is monitored by comparing a measurement of the NO and/or NO marker to a NO threshold. The NO threshold may be a safety limitation that ensures that methemoglobinemia does not develop. For example, the NO threshold may be a methemoglobin level, such as a percentage of methemoglobin relative to the red blood cells. In exemplary embodiments, the NO threshold is in the range from about 1% to about 15% methemoglobin, or about 3% to about 10% methemoglobin. Accordingly, the NO administration may be adjusted if the methemoglobin levels meet or exceed an acceptable range, such as 10%, 11% or 12%.

Similarly, other parameters such as indicators of tissue damage may be monitored. Examples of indicators of tissue damage include the liver enzymes aspartate aminotransferase (AST) and alanine aminotransferase (ALT). Another example includes serum creatinine, which is an indicator of tissue damage in the kidneys. Further examples include troponin and creatine kinase MB (CK-MB), which are indicators of heart damage. Other indicators of tissue damage are known in the art, such as creatine phosphokinase (CPK). An increase in an indicator of tissue damage may signal a need to decrease the delivery of NO.

Furthermore, other parameters may also be monitored. For example, additional relevant parameters for lungs include pulmonary vascular resistance (PVR) or other related measurements such as pulmonary capillary wedge pressure (PCWP), mean pulmonary arterial pressure (mPAP) and cardiac output (CO). NO delivery to lungs may be adjusted to obtain a desired drop in PVR or ensure that PVR does not drop below a certain threshold.

The NO and/or NO marker and/or other parameter may be monitored either continuously or intermittently, such as at regular intervals. The NO and/or NO marker and/or other parameter may be taken as the result of a single measurement or an average of measurements from different locations or at different times.

The NO administration may also be adjusted continuously or intermittently. The oxygen administration may be administered continuously or intermittently and may be adjusted continuously or intermittently.

The level of NO2 may also be monitored in the ex vivo fluid. NO2 may build up in the fluids due to recirculation of the fluids. If the NO2 concentration rises above a certain threshold, NO delivery device may adjust the NO administration and/or provide an alarm. The NO2 may also be removed through the use of a reducing agent, scrubber, base, or other appropriate means.

Instead of or in addition to adjusting the NO concentration, the NO administration may be adjusted by any means for adjusting the amount of NO that is delivered to the ex vivo fluid, such as by adjusting the flow rate of NO-containing gas that is delivered to the ex vivo fluid. The flow rate of NO-containing gas may be, for example, 5 mL/min, 10 mL/min, 15 mL/min, 20 mL/min, 25 mL/min, 30 mL/min, 40 mL/min, 50 mL/min, 60 mL/min, 70 mL/min, 80 mL/min, 90 mL/min, 0.1 L/min, 0.15 L/min, 0.2 L/min, 0.25 L/min, 0.3 L/min, 0.35 L/min, 0.4 L/min, 0.45 L/min, 0.5 L/min, 0.55 L/min, 0.6 L/min, 0.65 L/min, 0.7 L/min, 0.75 L/min, 0.8 L/min, 0.85 L/min, 0.9 L/min, 1 L/min, 1.25 L/min, 1.5 L/min, 1.75 L/min, 2 L/min, 2.5 L/min, 3 L/min, 3.5 L/min, 4 L/min, 4.5 L/min, 5 L/min, 5.5 L/min, 6 L/min, 6.5 L/min, 7 L/min, 8 L/min, 9 L/min or 10 L/min. The flow rate may be adjusted in incremental amounts, such as in increments in 5 mL/min, 10 mL/min, 15 mL/min, 20 mL/min, 25 mL/min, 30 mL/min, 40 mL/min, 50 mL/min, 60 mL/min, 70 mL/min, 80 mL/min, 90 mL/min, 0.1 L/min, 0.15 L/min, 0.2 L/min, 0.25 L/min, 0.3 L/min, 0.35 L/min, 0.4 L/min, 0.45 L/min, 0.5 L/min, 0.55 L/min, 0.6 L/min, 0.65 L/min, 0.7 L/min, 0.75 L/min, 0.8 L/min, 0.85 L/min, 0.9 L/min, 1 L/min, 1.25 L/min, 1.5 L/min, 1.75 L/min, 2 L/min, 2.5 L/min, 3 L/min, 3.5.

L/min, 4 L/min, 4.5 L/min, 5 L/min, 5.5 L/min, 6 L/min, 6.5 L/min, 7 L/min, 8 L/min, 9 L/min or 10 L/min. The flow rate may also be adjusted by a certain percentage relative to the last flow rate. Such incremental percentages can include 5%, 10%, 15%, 20%, 25%, 30%, 35%, 40%, 45%, 50%, 55%, 60%, 65%, 70%, 75%, 80%, 85%, 90%, 95%, 100%, 110%, 125%, 150%, 175% and 200% changes in the flow rate of the NO-containing gas.

The device for introduction of NO-containing gas into the ex vivo fluid may comprise a container, gas cylinder or receptacle for holding or locally generating the NO-containing gas, referred to as an "NO generator/receptacle". The device for introduction of the NO-containing gas into the ex vivo fluid will typically include a pump, injector or metering device to facilitate delivery of the NO-containing gas into the ex vivo fluid, referred to as an "NO delivery device".

The NO delivery device may include any appropriate components for administering NO to the ex vivo fluid, including flow sensors, valves, flow controllers, processors, safety shut-off valves, purge valves, etc. The NO delivery device may also include components for monitoring the gas that is administered to the fluid, such as gas concentration sensors (e.g. O2, NO and/or NO2 sensors), sampling pumps, etc. The NO delivery device may also include redundant sensors and/or valves and have an automatic backup delivery system in case of failure of the primary NO delivery system. The NO delivery device may also include one or more sensors for feedback control of the NO delivery and/or for independent safety monitoring of NO delivery. The NO delivery device can also provide alarms if any of the monitored parameters meet or exceed a certain level or if other safety issues are present. The NO delivery device may also include fluid flow or pressure sensors that are placed near the NO injection point, or integrated into the NO injection point, so that NO may only be injected when fluid is moving through the system or organ.

The NO delivery device may be portable and light (<10 lbs) so that it does not hinder the transport process and can be able to mount to existing transport boxes. The NO delivery device may run on a battery and have a battery life that meets a certain minimum criteria, such as having a battery life of at least 16 hours. The NO delivery device may also include a backup battery or other power source.

The NO source may include two or more gas cylinders such that continuous NO administration is not interrupted when one of the gas cylinders is replaced.

The NO delivery device may also include an automated pre-use checkout procedure with automatic purge to clear NO2, and on-screen setup instructions. The system may also have on-screen alarm help, and wireless connectivity to communicate with an electronic medical record (EMR) system or a tech support desk for remote troubleshooting. Another safety feature may be the incorporation of sensors and mechanisms to automatically detect fluid or gas leaks.

As set forth above, the NO delivery device may be in communication with a monitoring device, and the NO delivery device may adjust the NO administration based on the monitoring of the NO and/or NO marker and/or other parameter. The monitoring device may be part of or integrated with the NO delivery device, or it may be a separate component from the NO delivery device A device may also be used to monitor the microcirculation of a tissue, organ or organism. The microcirculation monitoring device may measure the partial pressure of carbon dioxide (PCO2) in the desired tissue, organ or organism. The microcirculation monitoring device may be part of or integrated into the NO delivery device, or may be monitored by a component separate from the NO delivery device. The microcirculation may be monitored continuously or intermittently, The NO delivery device may adjust the NO administration in response to changes in the microcirculation. For example, if the microcirculation restructuring increases, the NO dose may be increased. The device may also include at least one redundant microcirculation monitoring sensor that is independent from delivery control, or another monitoring mechanism to ensure patient safety. Such redundant sensors may help prevent overdosing or under-dosing in the event of a microcirculation sensor failure In certain embodiments, methods, compositions, and devices of the present invention are used to treat or prevent any of a variety of diseases and disorders that benefit from treatment with NO. In particular embodiments, the methods of the present invention may be used to modulate biological pathways regulated or affected by NO.

NO mediates vasodilation and can impact inflammatory responses, among other biological processes. Accordingly, diseases, disorders or conditions including conditions of interest in a subject or organ of a subject, or the blood of a subject, may be potentially treatable by administration of NO gas directly into ex vivo fluid according to the invention include respiratory, cardiovascular, pulmonary, and blood diseases, disorders or conditions, as well as hypoxemia, tumors, infections, inflammation, shock, ischemia-reperfusion injury, sepsis and stroke. In specific examples, respiratory distress syndrome, asthma, bronchospastic disease, myocardial infarction, hemorrhage, sickle cell disease, platelet aggregation and major surgery may be treatable according to the methods of the invention. Further specific examples include pulmonary hypertension and hypoxemia following cardiopulmonary bypass, mitral valve replacement, heart or lung transplantation, and pulmonary embolism. The NO may also be used in ECMO circuits and/or in any aspect of the organ transplant process. NO may also be used in cardiopulmonary bypass. Another example includes using NO to prevent and/or treat microcirculation alteration.

Administration of NO gas into ex vivo fluid may be useful in suppressing, killing, and inhibiting pathogenic cells, such as tumor/cancer cells, or microorganisms, including but not limited to pathogenic bacteria, pathogenic mycobacteria, pathogenic parasites, and pathogenic fungi. Examples of microorganisms include those associated with a respiratory infection within the respiratory tract.

Administration of NO gas into ex vivo fluids may enhance the survivability of biological materials, e.g., organs and tissues, that are subjected to ischemic or hypoxic conditions. In related embodiments, the present invention provides methods of preventing or reducing damage to biological materials, e.g., including cell, organ or tissue injuries resulting from ischemia or hypoxia. It is understood that a whole biological material or only a portion thereof, e.g., a particular organ, may be subjected to ischemic or hypoxic conditions.

The ischemic or hypoxic conditions may be the result of an injury or disease suffered by an organism. Examples of specific diseases that can induce ischemia or hypoxia include, but are not limited to, traumatic injury or surgery, respiratory or cardiac arrest, tumors, heart diseases, and neurological diseases. Examples of specific injuries that can result in ischemic or hypoxic conditions include, but are not limited to, external insults, such as burns, cutting wounds, amputations, gunshot wounds, or surgical trauma. In addition, injuries can also include internal insults, such as stroke or heart attack, which result in the acute reduction in circulation. Other injuries include reductions in circulation due to non-invasive stress, such as exposure to cold or radiation, or a planned reduction in circulation, e.g., during heart surgery.

In certain embodiments, methods of the present invention include administering NO-containing gas into ex vivo fluid prior to development of a disease, disorder or condition treatable with NO gas, e.g., prior to an ischemic or hypoxic injury or disease insult. Examples of such situations include, but are not limited to, major surgery where blood loss may occur spontaneously or as a result of a procedure, cardiopulmonary bypass in which oxygenation of the blood may be compromised or in which vascular delivery of blood may be reduced (as in the setting of coronary artery bypass graft (CABG) surgery), or in the treatment of organ donors prior to removal of donor organs for transport and transplantation into a recipient. Other examples include, but are not limited to, medical conditions in which a risk of injury or disease progression is inherent (e.g., in the context of unstable angina, following angioplasty, bleeding aneurysms, hemorrhagic strokes, following major trauma or blood loss).

In certain embodiments, methods of the present invention include administering NO-containing gas into ex vivo fluid after development or onset of a disease, disorder or condition treatable with NO, e.g., after an ischemic or hypoxic injury or disease insult, or after onset any of the diseases, disorders or conditions discussed above. In a particular aspect of such embodiments, NO-containing gas may be administered to a patient suffering from the disease, disorder or condition upon recognition or diagnosis of the disease, disorder or condition.

In certain embodiments, inflammatory-related diseases or disorders may be treated by administration of NO-containing gas directly into ex vivo fluid. Inflammatory-related diseases or disorders which may be treatable by the methods of the present invention include, e.g., multiple sclerosis, arthritis, rheumatoid arthritis, systemic lupus erythematosus, graft versus host disease, diabetes, psoriasis, progressive systemic sclerosis, scleroderma, acute coronary syndrome, Crohn's Disease, endometriosis, glomerulonephritis, myasthenia gravis, idiopathic pulmonary fibrosis, asthma, acute respiratory distress syndrome (ARDS), vasculitis, and inflammatory autoimmune myositis.

In one or more embodiments, the methods of the invention comprise administration of NO-containing gas directly into blood in an extracorporeal oxygenation system. The extracorporeal oxygenation system may be, for example, an extracorporeal membrane oxygenation (ECMO) system. In such methods the NO-containing gas is administered into the blood at any point in the ECMO circuit. In some embodiments, the NO is administered to arterialized blood, which is after oxygenation of the withdrawn blood. However, the NO may be administered in other points of the circuit, such as before oxygenation, or may be administered at multiple locations in the circuit. An exemplary ECMO circuit 100 according to the invention is illustrated in FIG. 1. Venous blood is withdrawn from the patient through venous cannula 105, which may be inserted in the right atrium, vena cava or femoral vein. Withdrawn venous blood is collected in reservoir 110 and circulated into membrane oxygenator 115 by pump 120. The membrane oxygenator removes $CO_2$ and oxygenates the blood before the blood is passed through heat exchanger 130. Oxygen is supplied to the membrane oxygenator 115 by oxygen source 117, which can be air, an oxygen blender, oxygen concentrator, or any other source of an oxygen-containing gas. The oxygenated blood is generally filtered through filter 135 prior to return to the body via arterial cannula 140, which may be inserted in the ascending aorta or the femoral artery. Alternatively, the cannula 140 may be a venous cannula for veno-venous (VV) ECMO. Heparin source 121 and fluid source 123 may be used to add anticoagulants and additional fluids, respectively, to the ECMO circuit. Non-heparin anticoagulants may also be used.

NO-containing gas may be introduced into the ECMO circuit via NO delivery device 145 which is in fluid communication with NO generating device/NO reservoir 150 and membrane oxygenator 115. NO-containing gas may be introduced into the ECMO circuit at any point in the circuit prior to return to the arterial circulation in the body. In the ECMO circuit illustrated in FIG. 1, this includes introduction before membrane oxygenator 115, in the membrane oxygenator 115, between oxygenator 115 and filter 135 or between filter 135 and arterial cannula 140. As shown in FIG. 1, NO may be administered in the membrane oxygenator 115 such that the NO and O2 are administered at the same time, or the NO may be added in the membrane oxygenator 115 at any time after the blood is oxygenated. In some embodiments the NO is added shortly after the blood is oxygenated.

The pressure is measured in the ECMO circuit in at least two places, such as by first pressure sensor 155 and second pressure sensor 160. Pressure sensors 155 and 160 may be placed in various locations in the ECMO circuit, such as before and after the membrane oxygenator and any filter(s). The difference in pressure readings between pressure sensor 155 and pressure sensor 160 provides a pressure drop in the ECMO circuit. This pressure drop may become unacceptably high due to clogging, and thus NO administration may reduce the clogging and associated pressure drop by platelet deactivation.

In one or more embodiments, the pressure sensors 155 and 160 are in direct or indirect communication with the NO delivery device. The NO delivery device may compare the pressure sensor measurements from the two pressure sensors to determine a pressure drop in the ECMO circuit, or a separate component in the ECMO circuit may determine the pressure drop and communicate the pressure drop to the NO delivery device. The NO delivery device may compare the pressure drop to a pressure drop threshold and adjust the NO delivery based on this comparison. If the pressure drop meets or exceeds the pressure drop threshold, the NO delivery device may increase the NO delivery concentration to reduce clogging in the ECMO system. The target pressure drop in an ECMO circuit is typically 2-6%, but may vary between various ECMO circuits. Accordingly, the pressure drop threshold may be in the range from 1% to 30% relative to the maximum pressure in the ECMO circuit or relative to the higher reading between the two pressure sensors. Exemplary pressure drop thresholds include, but are not limited to, 1%, 1.5%, 2%, 2.5%, 3%, 3.5%, 4%, 4.5%, 5%, 5.5% 6%, 7%, 8%, 9%, 10%, 15%, 20%, 25% and 30%.

In addition to administering NO to the blood, the NO delivery device may also monitor NO and/or a NO marker in the blood. Alternatively, the NO and/or NO marker may be monitored by a component separate from the NO delivery device.

The NO and/or NO marker may be monitored at any number of points within the ECMO circuit. Such locations include, but are not limited to, before oxygenation, after oxygenation and before NO administration, after NO administration but before re-introduction into the patient's circulatory system, and/or after re-introducing the blood into the patient's system. The NO and/or NO marker may be measured by sampling a portion of the blood from the circuit, such that a sample is removed from the circuit and analyzed. The sample size may be a very small amount. The NO and/or NO marker may also be measured directly in the blood circulating in the circuit. This can be accomplished by utilizing a capable sensor without removing blood from the circuit. For example, a pulse oximeter may be wrapped around the tube carrying the ex vivo blood or a probe may be placed in the blood flow. In the exemplary embodiment shown in FIG. 1, the NO marker is measured by the monitoring device 125 shortly before the ex vivo blood is reintroduced into the patient. Furthermore, the NO and/or NO marker may be monitored based on a single measurement, or an average of measurements from different locations or different times.

Figure 2:
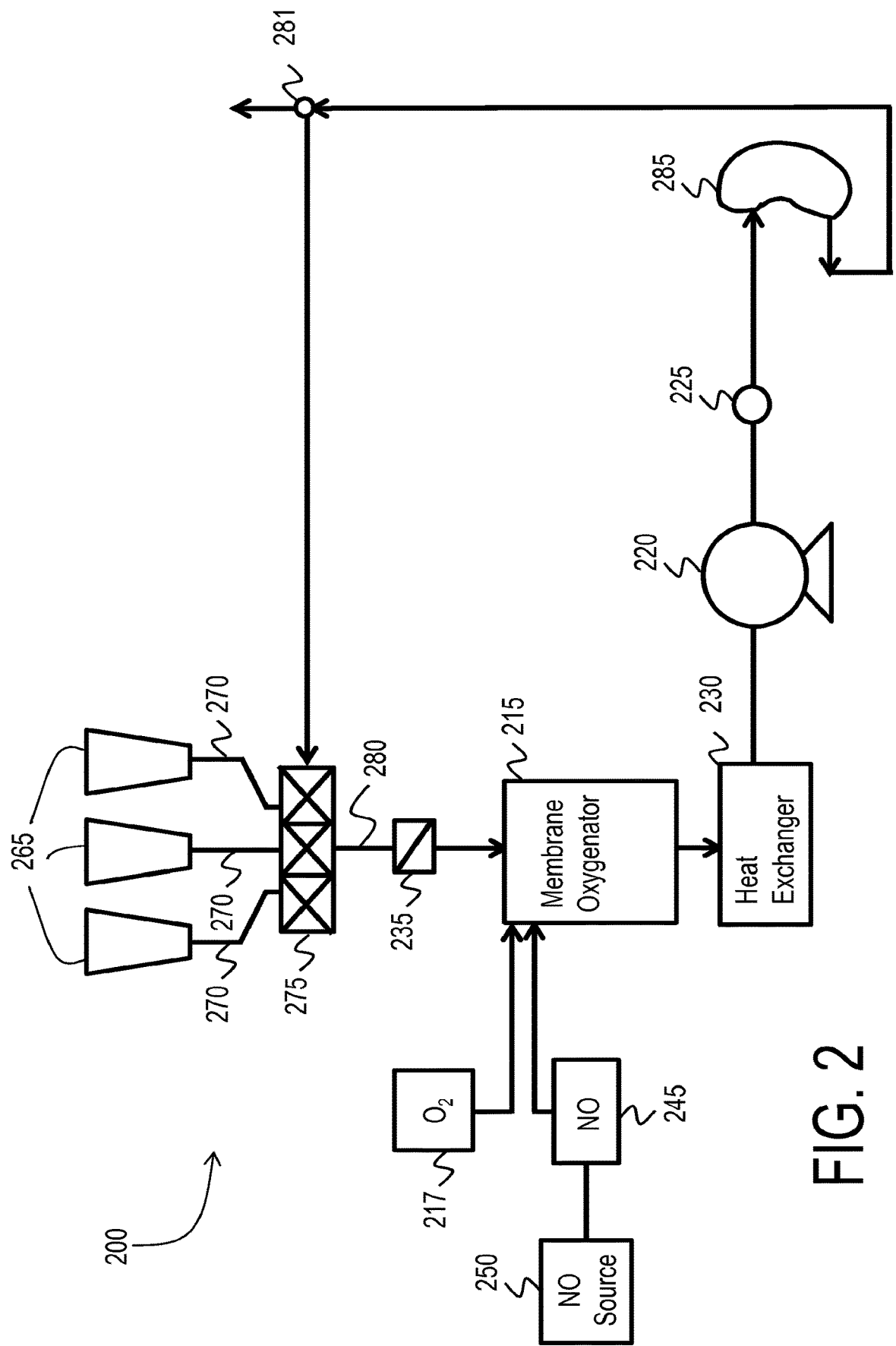
FIG. 2 illustrates an exemplary organ perfusion circuit that can be used in accordance with one or more embodiments of the invention.

NO may also be administered and monitored in perfusion fluid for preserving organs or other biological material for transplant. FIG. 2 illustrates an exemplary organ perfusion circuit 200. One or more reservoirs 265 provide various components for the perfusion fluid. Each reservoir 265 is in fluid communication with a conduit 270 for carrying the respective components. A valve system 275 meters the components from the various conduits 270 to a common conduit 280 to provide the perfusion fluid for the perfusion circuit. As described above, the perfusion fluid may contain any known components, including red blood cells, salts, preservatives, etc. One or more filters 235 may be used before and/or after entering the membrane oxygenator 215. The membrane oxygenator 215 removes CO2 and oxygenates the perfusion fluid. Oxygen is supplied to the membrane oxygenator 215 by oxygen source 217, which can be air, an oxygen blender, oxygen concentrator, or any other source of an oxygen-containing gas. The perfusion fluid may be warmed and/or cooled by one or more heat exchangers 230. A pump 220 provides the oxygenated perfusion fluid to the organ 285.

A NO delivery device 245 may be used to introduce NO-containing gas from a NO generating device/NO reservoir 250. NO-containing gas may be introduced into the organ perfusion circuit at any point in the circuit. In the organ perfusion circuit illustrated in FIG. 2, this includes introduction before the membrane oxygenator 215, in the membrane oxygenator 215, or between the membrane oxygenator 215 and organ 285.

The NO and/or NO marker and/or other parameter may be monitored at any number of points within the perfusion circuit. Such locations include, but are not limited to one or more of, before oxygenation, after oxygenation and before NO administration, after NO administration but before exposure to the organ, and/or exposing the organ to the perfusion fluid. The NO and/or NO marker and/or other parameter may be measured by sampling a portion of the perfusion fluid from the circuit, such that a sample is removed from the circuit and analyzed. The sample size may be a very small amount. The NO and/or NO marker and/or other parameter may also be measured directly in the perfusion circulating in the circuit. This can be accomplished by utilizing a capable sensor without removing perfusion fluid from the circuit. In the exemplary embodiments shown in FIG. 2, monitoring device 225 measures the NO marker shortly before the perfusion fluid is delivered to the organ 285. A monitoring device may also comprise a probe placed in the perfusion fluid and/or organ that can provide real-time measurements of NOx levels, etc. Furthermore, in addition to or as an alternative to measuring NO and/or NO marker and/or other parameter in the perfusion fluid, any of these parameters may be measured directly in the organ. Furthermore, the NO and/or NO marker and/or other parameter may be monitored based on a single measurement, or an average of measurements from different locations or different times.

The perfusion fluid may recirculate through the perfusion circuit, or some or all of the perfusion fluid may be removed as part of a purge or bleed at point 281. For example, the fluid bled at point 281 may be a certain volumetric percentage of the fluid in conduit 280, and may range from 0% (no bleed, complete recirculation) to 100% (complete bleed, no recirculation). Exemplary bleed percentages include 0%, 0.5%, 1%, 2%, 5%, 10%, 15%, 20%, 25%, 30%, 40%, 50%, 60%, 70%, 80%, 90%, 95%, 97%, 98%, 99%, 99.5% A and 100% by volume. In some embodiments, providing a bleed greater than 0% can reduce the buildup of byproducts in the perfusion fluid, such as the buildup of NOx compounds as a result of NO delivery to the perfusion fluid.

As an alternative to a continuous bleed, all or a portion of the fluid may be removed and replaced at certain intervals. As a result of the sudden change in NO and/or NO marker that can occur from the removal and replacement, the NO delivery device may administer a large amount of NO in a short period of time to raise the in NO and/or NO marker back to a desired level. This NO adjustment may occur automatically as part of the feedback loop between the NO delivery device and the monitoring of NO and/or NO marker The organ perfusion circuit described herein can be utilized with any biological material in need of NO administration or in need of preventing and/or treating ischemia-reperfusion injury. The biological material may include cells, tissue, or a partial or complete organ. The organs, tissue, and/or cells may be for any suitable type for transplant, including hearts, lungs, kidneys, livers pancreases, eyes, bones, skin, heart valves, bowels, tendons, ligaments or veins, or any portion or cells derived therefrom. In particular embodiments, the organ may be a liver. In other particular embodiments, the organ may be one or more lungs. In other particular embodiments, the organ may be a heart.

In one or more embodiments, it may be advantageous to flush the organ or biological material prior to implanting into a recipient. For example, after terminating NO administration to the organ or biological material, flushing the organ or biological material may help remove residual NO and/or NO-related byproducts from the organ or biological material so that these compounds are not remaining and introduced into the recipient. Techniques for flushing organs and biological materials can include any that are known in the art.

Furthermore, other preservation techniques may be used in addition to or instead of perfusion. For example, persufflation is an organ preservation technique in which an organ is perfused with a gas such as an oxygen-containing gas. The gas may be introduced into the organ through a blood vessel such as a vein, and the organ may be punctured to allow gas to escape through the holes. Another organ preservation technique is ventilation, wherein ex vivo lungs are ventilated with a respiratory gas, which can simulate respiration in in vivo lungs. Either of these techniques may be combined with organ perfusion, as will be described in more detail below.

Figure 3:
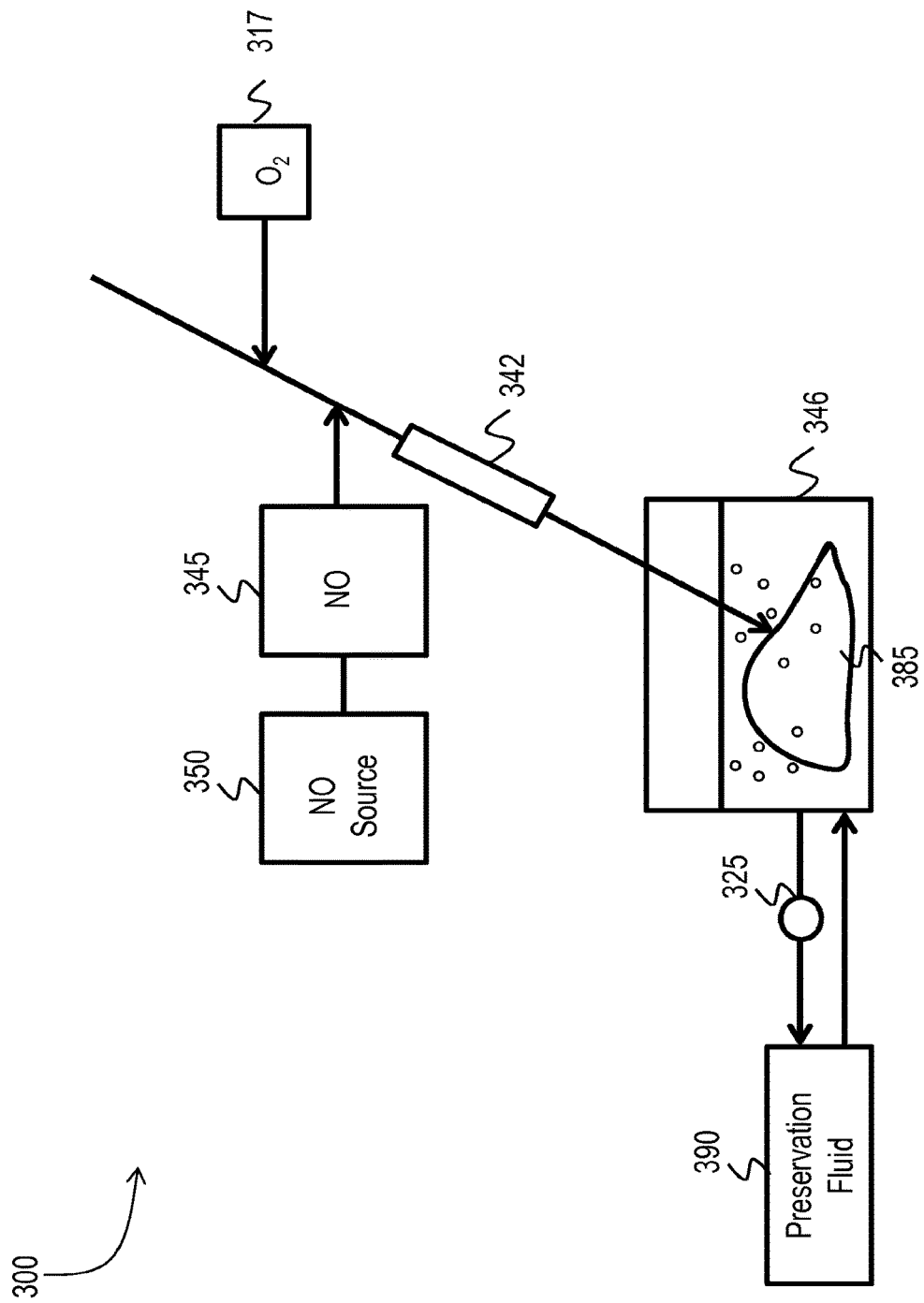
FIG. 3 illustrates an exemplary system for persufflating a liver that can be used in accordance with one or more embodiments of the invention.

FIG. 3 shows an exemplary system 300 for persufflating an organ 385. As shown in FIG. 3, the organ 385 may be a liver. The organ 385 may be stored in a container 346, which may be filled with a preservation fluid. The preservation fluid can be any liquid suitable for storing an organ, such as perfusion fluid as described above. Persufflation gas is introduced into the organ 385 via a catheter 342, which may inject the persufflation gas into the existing vasculature of the organ 385. For example, the persufflation gas may be injected into the suprahepatic vena cava.

The preservation fluid used to store the organ 385 during persufflation may be monitored and/or regulated by a preservation fluid device 390. For example, the preservation fluid device 390 may remove a portion of the preservation fluid, and regulate the composition of the preservation fluid by removing byproducts from the preservation fluid and/or adding fresh preservation fluid and/or add desired components to the preservation fluid. The preservation fluid device 390 can include any of the features of any organ perfusion circuit described above, including pumps, filters, heat exchanges, membrane oxygenators, sources for components for the preservation fluid, etc. NO may also be administered to the preservation fluid according to the methods described herein.

The persufflation gas injected to the organ 385 may comprise air, supplemental oxygen and/or nitric-oxide containing gas, as well as inert carrier gases such as nitrogen. For example, an oxygen source 317 can be used to introduce O2 into the gas used for persufflation. A NO delivery device 345 which is in fluid communication with NO generating device/NO reservoir 350 may be used to introduce NO into the persufflation gas. However, if the persufflation gas already includes NO, then it may not be necessary to deliver NO to the persufflation gas.

In various embodiments, the concentration of oxygen in the persufflation gas may be about 0%, about 10%, about 20%, about 30%, about 40%, about 50%, about 60%, about 70%, about 80%, about 90%, about 95%, about 98%, about 99% or up to about 100%. The NO concentration in the persufflation gas may be any of the ranges described above, such as from 0.1 ppm to 300 ppm.

In one or more embodiments, the concentration of NO and/or a NO marker and/or other parameter is measured in the preservation fluid, and the concentration of NO in the persufflation gas is adjusted based on the measurement of the NO and/or NO marker and/or other parameter. Any of the monitoring and adjustment procedures described above for ex vivo fluids may be applied to monitoring and adjustment of NO during persufflation. The NO and/or a NO marker and/or other parameter in the preservation fluid may be measured by the preservation fluid device 390 and/or may be measured by the NO delivery device 345 and/or may be measured by a monitoring device 325. The monitoring device 325 may have any of the features described above. For example, NO and/or NO markers may be measured directly through techniques such as pulse oximetry or optical measurement or any other means for measuring or co-relating NO and/or NO markers either directly or indirectly. As another example, a probe may be placed in the preservation fluid to measure fluid NOx levels and may provide real-time analysis of the preservation fluid. As shown in FIG. 3, the monitoring device 325 may measure the NO and/or NO marker in preservation fluid that has been drawn out of the container 346, and/or the monitoring device 325 may measure the NO and/or NO marker in the preservation fluid while it is in the container 346. The monitoring device 325 may be in communication with the NO delivery device 345. Furthermore, in addition to or as an alternative to measuring NO and/or NO marker and/or other parameter in the preservation fluid, any of these parameters may be measured directly in the organ. If the parameters are measured directly in the organ, then it may be advantageous to make measurements at several different locations in the organ because different parts of the organ may have different localized conditions. These different measurements may be averaged or individually monitored according to any of the monitoring methods described herein.

The organ (e.g. liver) may also be perfused before or after persufflation. Such perfusion may incorporate any of the features described above.

Figure 4:
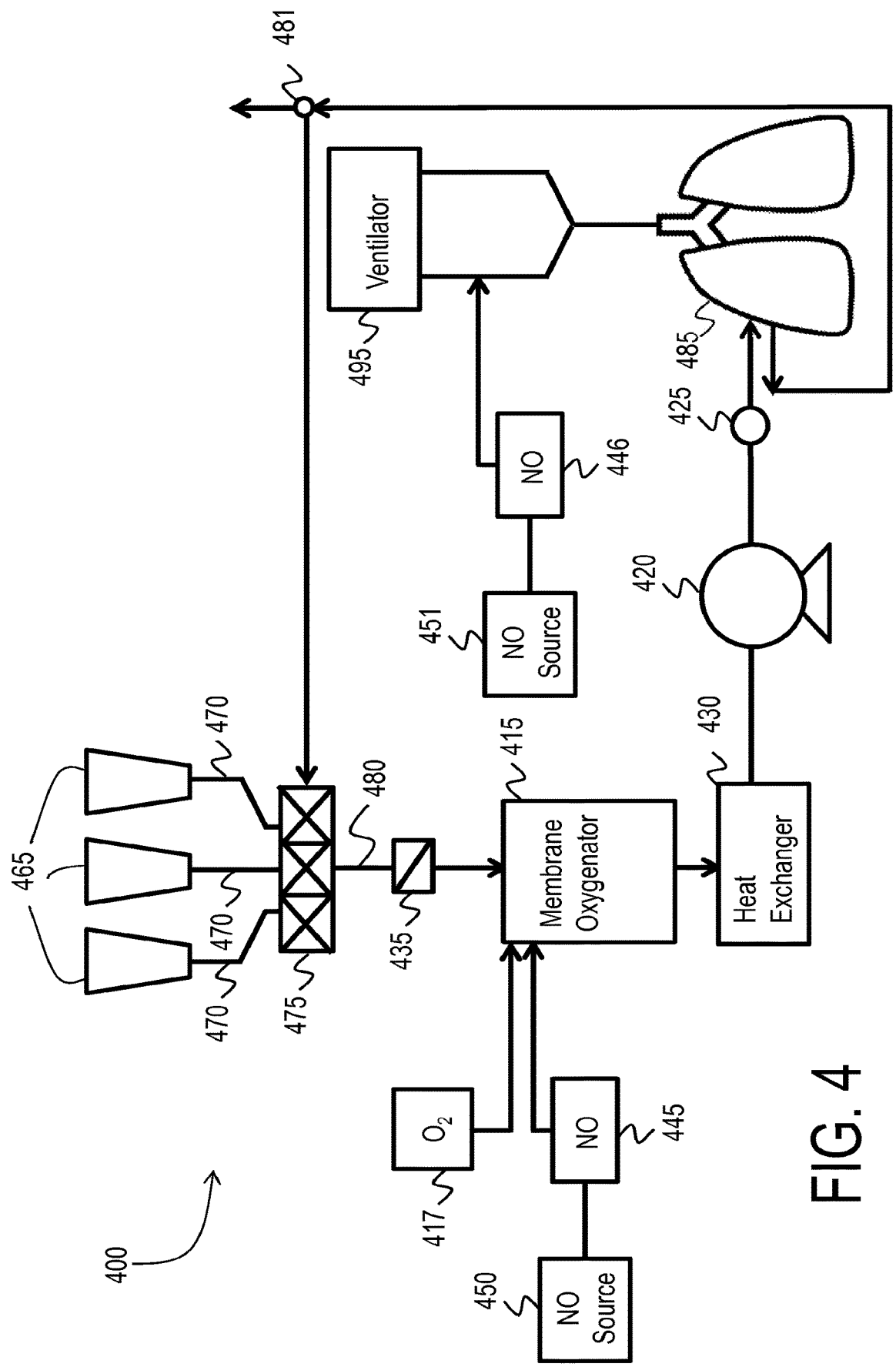
FIG. 4 illustrates an exemplary system for ventilating lungs that can be used in accordance with one or more embodiments of the invention.

If the organ for preservation is one or more lungs, the lungs may be ventilated during perfusion. Any exemplary system 400 for ventilating and perfusing lungs is shown in FIG. 4. However, it is also possible for the lungs only to be ventilated or only to be perfused, or for the lungs to be perfused and ventilated sequentially instead of simultaneously.

One or more reservoirs 465 provide various components for the perfusion fluid. Each reservoir 465 is in fluid communication with a conduit 470 for carrying the respective components. A valve system 475 meters the components from the various conduits 470 to a common conduit 480 to provide the perfusion fluid for the perfusion circuit. As described above, the perfusion fluid may contain any known components, including red blood cells, salts, preservatives, etc. One or more filters 435 may be used before and/or after entering the membrane oxygenator 415. The membrane oxygenator 415 removes CO2 and oxygenates the perfusion fluid. Oxygen is supplied to the membrane oxygenator 415 by oxygen source 417, which can be air, an oxygen blender, oxygen concentrator, or any other source of an oxygen-containing gas. The perfusion fluid may be warmed and/or cooled by one or more heat exchangers 430. A pump 420 provides the oxygenated perfusion fluid to the lungs 485.

A NO delivery device 445 may be used to introduce NO-containing gas from a NO generating device/NO reservoir 450. NO-containing gas may be introduced into the organ perfusion circuit at any point in the circuit. In the organ perfusion circuit illustrated in FIG. 4, this includes introduction before the membrane oxygenator 415, in the membrane oxygenator 415, or between the membrane oxygenator 415 and lungs 485. However, if the perfusion fluid already includes NO and/or a NO donor, then it may not be necessary to deliver NO to the ventilation gas.

As shown in FIG. 4, the lungs 485 may be ventilated by a ventilator 495 or other device that provides a respiratory gas to the lungs 485. The ventilation gas may be carried from the ventilator 495 to the lungs 485 via any appropriate conduits and/or tubing.

Various ventilation strategies may be employed. For example, the lungs may be ventilated by supplying ventilation gas with a positive pressure (above atmospheric pressure). Another example includes utilizing a negative pressure (below atmospheric pressure) around the lungs to allow the lungs to naturally fill with ventilation gas that is at or near atmospheric pressure. These strategies may also be combined by supplying positive-pressure ventilation gas to the lungs and utilizing a negative pressure around the lungs.

Also, according to one or more embodiments, the lungs may be placed in several possible positions during ventilation and/or perfusion. In current methods, lungs are typically placed on their sides during ventilation and/or perfusion. However, such placement may cause undue pressure on certain portions of the lungs, and can lead to localized pulmonary hypertension and/or tissue damage. Accordingly, one or more embodiments of the present invention provide that the lungs are positioned in a more "natural" position that is similar to the lungs' position when in a living organism. For example, the lungs may be suspended in a vertical position by placing the lungs in a solution or gel that has an appropriate density to maintain the lungs in the vertical position. Other possible methods for suspending the lungs include packing the lungs in a material that distributes the pressure over a large area of the lungs. The lungs may also be hung in a bag or netting, or may be hung by the trachea. These various methods of suspending the lungs in the natural position may also be combined.

The ventilation gas may be an oxygen-containing gas, such as air with or without supplemental oxygen. As with the persufflation gas described above, the concentration of oxygen in the ventilation gas may be about 0%, about 10%, about 20%, about 30%, about 40%, about 50%, about 60%, about 70%, about 80%, about 90%, about 95%, about 98%, about 99% or up to about 100%.

The ventilation gas may also contain NO. The NO concentration in the ventilation gas may be any of the ranges described above, such as from 0.1 ppm to 300 ppm. However, if the ventilation gas already includes NO, then it may not be necessary to deliver NO to the ventilation gas.

In various embodiments, the concentration of NO and/or a NO marker and/or other parameter is measured in the perfusion fluid and/or in the ventilation gas and/or directly in the lungs. The NO and/or NO marker and/or other parameter may be monitored at any number of points within the perfusion circuit or within the ventilation circuit. For measuring the NO and/or NO marker and/or other parameter in the perfusion fluid, such locations include, but are not limited to, before oxygenation, after oxygenation and before NO administration, after NO administration but before exposure to the lungs, and/or after exposing the lungs to the perfusion fluid. The NO and/or NO marker and/or other parameter may be measured by sampling a portion of the perfusion fluid from the circuit, such that a sample is removed from the circuit and analyzed. The sample size may be a very small amount. The NO and/or NO marker and/or other parameter may also be measured directly in the perfusion circulating in the circuit. This can be accomplished by utilizing a capable sensor without removing perfusion fluid from the circuit. In the exemplary embodiment shown in FIG. 4, monitoring device 425 measures the NO marker shortly before the perfusion fluid is delivered to the lungs 485. A monitoring device may also comprise a probe placed in the perfusion fluid and/or lungs that can provide real-time measurements of NOx levels, etc. The monitoring device 425 may be in communication with the NO delivery device 445 and/or the NO delivery device 446.

For measuring the NO and/or NO marker in the ventilation circuit, the NO and/or NO marker may be measured before the ventilation gas is delivered to the lungs and/or after the ventilation gas is delivered to the lungs.

For measuring one or more of these parameters in the lungs, NO and/or NO2 may be measured in the gas in the lungs. Other parameters may also be measured, such as PVR, PCWP, mPAP and/or CO, or indicators of tissue damage. If the parameters are measured directly in the lungs, then it may be advantageous to make measurements at several different locations in the lungs because different parts of the lungs may have different localized conditions. These different measurements may be averaged or individually monitored according to any of the monitoring methods described herein.

Based on the measurements of the NO and/or NO marker in the perfusion fluid and/or ventilation gases, the NO concentration in the ventilation gas and/or the NO administration to the perfusion fluid may be adjusted according to the methods described herein.

The perfusion fluid may recirculate through the perfusion circuit, or some or all of the perfusion fluid may be removed as part of a purge or bleed at point 481. For example, the fluid bled at point 481 may be a certain volumetric percentage of the fluid in conduit 480, and may range from 0% (no bleed, complete recirculation) to 100% (complete bleed, no recirculation). Exemplary bleed percentages include 0%, 0.5%, 1%, 2%, 5%, 10%, 15%, 20%, 25%, 30%, 40%, 50%, 60%, 70%, 80%, 90%, 95%, 97%, 98%, 99%, 99.5% and 100% by volume. In some embodiments, providing a bleed greater than 0% can reduce the buildup of byproducts in the perfusion fluid, such as the buildup of NOx compounds as a result of NO delivery to the perfusion fluid.

In addition to administering NO to perfusion fluid, persufflation gas and/or ventilation gas for an ex vivo organ, NO may be administered to either the organ donor and/or organ recipient to enhance the likelihood of success for the organ transplant. For example, it is believed that administration of inhaled nitric oxide (iNO) to the organ recipient will reduce primary graft dysfunction. If iNO is administered the organ recipient, the iNO may be administered before organ transplantation, during organ transplantation and/or after organ transplantation. In exemplary embodiments, the concentration of iNO administered to the donor and/or recipient may be in the range from about 1 ppm to about 80 ppm, such as about 1 ppm, about 2 ppm, about 3 ppm, about 4 ppm, about 5 ppm, about 6 ppm, about 7 ppm, about 8 ppm, about 9 ppm, 10 ppm, about 15 ppm, about 20 ppm, about 25 ppm, about 30 ppm, about 35 ppm, about 40 ppm, about 45 ppm, about 50 ppm, about 60 ppm, about 70 ppm, or about 80 ppm.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method of preserving an ex vivo liver for transplant comprising:
    persufflating the liver with a persufflation gas comprising nitric oxide (NO);
    monitoring one or more persufflation parameters in (i) the liver and/or (ii) a preservation fluid used to store the liver during persufflation; and
    adjusting the amount of NO provided to the liver by the persufflation gas based on the monitoring of the one or more persufflation parameters,
    wherein the one or more persufflation parameters includes an indicator of tissue damage, and
    wherein the indicator of tissue damage includes aspartate aminotransferase (AST), alanine aminotransferase (ALT), or combinations thereof.

2. The method of claim 1, wherein the concentration of NO in the persufflation gas is in the range from 0.1 ppm to 300 ppm.

3. The method of claim 1, wherein the persufflation gas further comprises oxygen, air, and/or carrier gases.

4. The method of claim 3, wherein the carrier gasses are nitrogen and/or helium.

5. The method of claim 1, wherein the monitoring is performed continuously or intermittently.

6. The method of claim 1, wherein the adjusting the amount of NO is performed continuously or intermittently.

7. The method of claim 1, further comprising perfusing the liver with a perfusion fluid comprising NO and/or a NO donor.

8. The method of claim 7, wherein the liver is perfused with the perfusion fluid before the liver is persufflated with the persufflation gas.

9. The method of claim 7, further comprising:
    monitoring one or more perfusion parameters in the perfusion fluid and/or in the liver itself; and
    adjusting the amount of NO and/or NO donor provided to the liver by the perfusion fluid based on the monitoring of the one or more perfusion parameters.

10. The method of claim 9, wherein the one or more perfusion parameters is selected from the group consisting of NO, a NO marker, an indicator of tissue damage, or combinations thereof.

11. The method of claim 9, wherein adjusting one or more of (i) the amount of NO provided to the liver by the persufflation gas or (ii) the amount of NO provided to the liver by the perfusion fluid comprises adjusting the NO concentration in a flow of gas delivered to the persufflation gas or perfusion fluid, respectively and/or adjusting the flow rate of the gas delivered to the persufflation gas or perfusion fluid, respectively.

12. The method of claim 9, wherein the perfusion fluid comprises red blood cells.

13. The method of claim 12, further comprising oxygenating the perfusion fluid before perfusing the liver.

14. The method of claim 9, wherein monitoring the NO marker in the perfusion fluid comprises monitoring methemoglobin.

15. The method of claim 9, wherein the viability of the liver is increased by the persufflation and/or perfusion with NO and/or NO donor when the NO administration is adjusted based on the monitoring of the one or more persufflation parameters and/or the one or more perfusion parameters.

* * * * *